United States Patent
Hagedorn et al.

(10) Patent No.: US 9,165,472 B2
(45) Date of Patent: Oct. 20, 2015

(54) ELECTROPHYSIOLOGY MEASUREMENT AND TRAINING AND REMOTE DATABASED AND DATA ANALYSIS MEASUREMENT METHOD AND SYSTEM

(71) Applicants: David W Hagedorn, Jacksonville, NC (US); James W. G. Thompson, New York, NY (US)

(72) Inventors: David W Hagedorn, Jacksonville, NC (US); James W. G. Thompson, New York, NY (US)

(73) Assignee: EVOKE NEUROSCIENCE, Jacksonville, NC (US)

( * ) Notice: Subject to any disclaimer, the term of this patent is extended or adjusted under 35 U.S.C. 154(b) by 0 days.

(21) Appl. No.: 14/215,431

(22) Filed: Mar. 17, 2014

(65) Prior Publication Data
US 2014/0288614 A1 Sep. 25, 2014

Related U.S. Application Data

(63) Continuation-in-part of application No. 13/742,066, filed on Jan. 15, 2013, now Pat. No. 8,838,247, which is a continuation of application No. 13/543,204, filed on Jul. 6, 2012, now Pat. No. 8,380,316, which is a continuation of application No. 12/979,419, filed on Dec. 28, 2010, now Pat. No. 8,239,030.

(60) Provisional application No. 61/791,649, filed on Mar. 15, 2013, provisional application No. 61/292,791, filed on Jan. 6, 2010.

(51) Int. Cl.
| | |
|---|---|
| *A61N 1/00* | (2006.01) |
| *G09B 5/00* | (2006.01) |
| *A61B 5/0482* | (2006.01) |
| *A61B 5/00* | (2006.01) |
| *A61N 1/36* | (2006.01) |
| *A61N 1/04* | (2006.01) |
| *A61N 1/20* | (2006.01) |

(52) U.S. Cl.
CPC .............. *G09B 5/00* (2013.01); *A61B 5/0006* (2013.01); *A61B 5/0482* (2013.01); *A61B 5/6803* (2013.01); *A61N 1/36025* (2013.01); *A61N 1/0484* (2013.01); *A61N 1/20* (2013.01)

(58) Field of Classification Search
CPC .............. A61B 5/0482; A61B 5/6803; A61N 1/36025; A61N 1/0484
See application file for complete search history.

(56) References Cited

U.S. PATENT DOCUMENTS

| | | | | |
|---|---|---|---|---|
| 2007/0150024 | A1* | 6/2007 | Leyde et al. | 607/45 |
| 2008/0262565 | A1* | 10/2008 | Bentwich | 607/45 |
| 2011/0035231 | A1* | 2/2011 | Firminger et al. | 705/2 |
| 2012/0296569 | A1* | 11/2012 | Shahaf et al. | 702/19 |

(Continued)

*Primary Examiner* — Robert N Wieland
(74) *Attorney, Agent, or Firm* — Timothy J. Bechen; Bechen PLLC

(57) ABSTRACT

A method and system provides for electrophysiological data analysis in a networked processing environment. The method and system includes receiving, via a networked connection, electrophysiological data of a patient and electronically performing, via at least one network processing device, a data analysis on the electrophysiological data. The method and system includes generating at least one report based on the data analysis, wherein the at least one report includes determination of one or more intervention options for the patient and therein transmitting the report to a recipient device across the network connection for utilization with the patient. The results of the report direct the user to apply from within the same system non-invasive brain stimulation, neurofeedback, and biofeedback modalities. Re-assessment can occur from within the same system following the training or modulation of electrophysiology and thereby generate a comparison report showing functional changes from the provided intervention or combined interventions.

22 Claims, 8 Drawing Sheets

(56) References Cited

U.S. PATENT DOCUMENTS

| | | | |
|---|---|---|---|
| 2013/0317580 A1* | 11/2013 | Simon et al. | 607/115 |
| 2014/0074179 A1* | 3/2014 | Heldman et al. | 607/45 |
| 2014/0296089 A1* | 10/2014 | Holmes et al. | 506/9 |
| 2014/0316248 A1* | 10/2014 | deCharms | 600/411 |

* cited by examiner

ID: 9,165,472 B2

ELECTROPHYSIOLOGY MEASUREMENT AND TRAINING AND REMOTE DATABASED AND DATA ANALYSIS MEASUREMENT METHOD AND SYSTEM

PRIORITY CLAIMS

The present Application is a Continuation-in-part of and claims priority to U.S. patent application Ser. No. 13/742,066 filed Jan. 15, 2013, issued as U.S. Pat. No. 8,838,247, which is a continuation of and claims priority to U.S. patent application Ser. No. 13/543,204, filed Jul. 6, 2012, issued as U.S. Pat. No. 8,380,316, which is a continuation of and claims priority to U.S. patent application Ser. No. 12/979,419, filed Dec. 28, 2010, issued as U.S. Pat. No. 8,239,030, which is based on and claims priority to U.S. Provisional Patent Application Ser. No. 61/292,791 filed Jan. 6, 2010.

The present Application further claims priority to U.S. Provisional Patent Application Ser. No. 61/791,649 filed Mar. 15, 2013.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF INVENTION

The disclosed technology relates generally to the assessment and remediation of abnormal brain and physiological functioning. More specifically, the technology relates to detection, assembling and management of data acquired based on the performance of electrophysiology testing.

BACKGROUND

Traumatic brain injuries can result in physical and/or emotional dysfunction. Post traumatic stress disorder (PTSD) symptoms are similar to those of a mild traumatic brain injury (mTBI) and the two are difficult to differentiate using current assessment methodologies such as symptom assessments and questionnaires. In Army deployment, statistics have shown that upwards of 20% of soldiers suffer from mild traumatic brain injury (mTBI). Head and neck injuries, including severe brain trauma, have been reported in one quarter of United States service members who have been evacuated from Iraq and Afghanistan in the first decade of the 21st century. A common cause of such injuries arises from exposure to percussive force from explosive devices. Further, recent military analysis indicates that over 90% of patients with acute mTBI will have vestibular (inner ear balance) disorders and those vestibular disorders are present in over 80% of persons with chronic mTBI symptoms. Likewise, stress disorders further affect numerous individuals, whether in a military or civilian situation. Brain injuries may further be incurred from car and bicycle accidents, sports accidents, falls, and the like. Up to 15% of persons suffering even a mild brain injury, or concussion, will suffer from persistent symptoms for more than a year, which significantly negatively affect their ability to work and function in daily life. It is estimated that there are currently 5.3 million Americans living with a disability as a result of a TBI. There are approximately 1.5 million diagnosed brain injuries in the U.S. annually, and it is estimated that another 2 million TBIs occur but are not properly diagnosed. Current assessment methods are either prohibitively expensive or do not diagnose the root cause of the suffering. Thus, there is a need in the art to accurately and quickly assess brain injury and associated dysfunction and then find ways to aid or enhance optimal functioning.

The brain is composed of about 100 billion neurons, more than 100 billion support cells and between 100 and 500 trillion neural connections. Each neuron, support cell and neural connection is extremely delicate, and the neural connections are tiny (approximately 1 micrometer). When the brain moves within the skull, such as occurs in rapid acceleration/deceleration (e.g., exposure to sudden impact and/or explosive devices), axons within the brain can pull, stretch and tear. If there is sufficient injury to the axon or support cells, the cell will die, either immediately or within a few days. Such damage can occur not only in the region that suffered direct trauma but in multiple regions (e.g., diffuse axonal injury). Loss of consciousness is not a prerequisite for mild traumatic brain injury and occurs in less than 5% of mild brain injuries, and head injuries such as diffuse axonal injury are not detectable in routine CT or MRI scan. High false negative findings may lead to patients being undiagnosed or misdiagnosed. Unfortunately current imaging methods still lack the resolution and sensitivity to determine functional brain capacity. Rating scales and other neuropsychological and functional examination methods have long been used to elucidate these functional questions, but they too are fraught with false negative results and limited specificity.

Problems exist in the collection and management of such large amounts of data. The performance of these measurements generate significant amounts of data, both personal in nature the patient, but in need of processing power to perform proper analysis of the data.

Wearable wireless transmitting physiology sensors and digital recording and processing of these human physiology measurements have permitted new technologies to measure and modify human physiology and to treat disorders from remote locations around the world.

Therefore, there are needs for insuring the security of such human data. Another need is the importance of mobile access to the testing and treatment and training data that is housed and managed with smart technology that both processes physiology data and allows access to individual interventions at any suitable location.

BRIEF DESCRIPTION

An object of the disclosed system and method of the present processing technology is to utilize a remote processing system that accepts electrophysiology and related data that is converted into usable reports and directed instructions to improve human functions. The system and method and underlying technology provides for the collection of physiology data for remote processing and returned feedback. Moreover, the method and system provides for account management tools relating to the data and operations associated with the data.

The system and method includes the collection of data using one or more data collection techniques. These techniques may include the performance of one or more tests using electrophysiology equipment, including wired and/or wireless equipment. The testing data is then collected, collated, assembled and may be pre-processed as necessary. The data is then transmitted to one or more central processing devices for the performance of processing operations thereon.

In the network-based or cloud-based processing technique, the data is processed and managed. Variety of processing operations are performed on the data to better understand and analyze the data, as well as catalog and centrally store the data.

Therein, the method and system further allows for networked access to the data, including access by any number one-number-of suitable parties. Access may include the patient's doctor reviewing the data for analysis purposes and the prescription of treatment orders.

Therefore, the present method and system allows for the detection and collection of physiology data, the networked transmission of the data, central processing of the data and the transmission to one or more users regardless of actual physical location.

In accordance with these and other objects, which will become apparent hereinafter, the disclosed technology will now be described with particular reference to the drawings.

A better understanding of the disclosed technology will be obtained from the following detailed description of the preferred embodiments taken in conjunction with the drawings and the attached claims.

DETAILED DESCRIPTION

Various embodiments are described herein, both directly and inherently. However, it is understood that the described embodiments and examples are not expressly limiting in nature, instead illustrate examples of the advantageous uses of the innovative teachings herein. In general, statements made in the specification of the present application do not necessarily limit any of the various claimed inventions and it is recognized that additional embodiments and variations recognized by one or more skilled in the art are incorporated herein.

As noted above, the present method and system provides for assembly and computational processing of physiology data, specifically electrophysiology data. The data is collected and processed in a networked or server-based processing environment, providing the offloading of the requisite processing requirements. The data is additionally managed in the secure network processing environment.

Embodiments of the disclosed technology process provide a combination of electroencephalography, electrocardiography, and non-invasive stimulation device usage and associated secure data processing and management. Upon measuring an electrical anomaly in a region of a brain or heart, real time wireless transmission occurs to one or more of a host local computer, remote computer or central processing unit from which database comparison and processing occurs in order to permit individual interventions and data analysis, local interventions and report review.

The present method and system expands the scope of data measurement by including active communication to external processing device(s) and/or system(s).

The present method and system provides to the measuring location comparison databases expanding the comparative ability of the measured data. In one embodiment, devices of the disclosed technology may utilize visual, balance, auditory, and other stimuli to test the subject, analyze necessary brain stimulations, and administer stimulation to the brain. Remote data processing, storage, data mining for further nervous system analysis, and merchant account management is embodied in the process of engineering computer logic, as described below.

Figure 1:
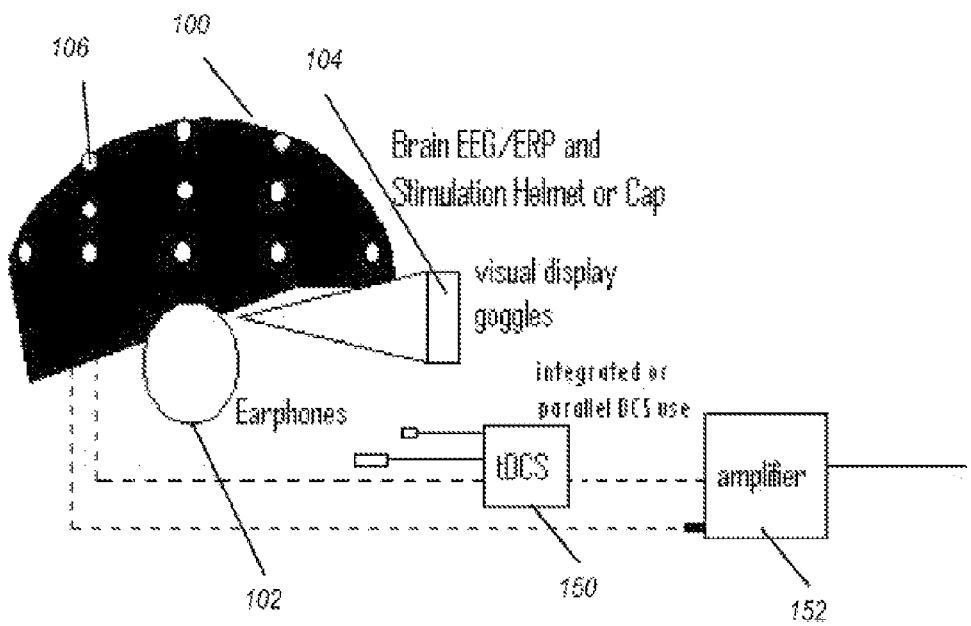
FIG. 1 illustrates one embodiment of a device for taking measurements.

FIG. 1 illustrates a measurement device used to measure the initial data. A helmet 100 comprises at least one, or a plurality of, electrodes 106 (represented as white dots). The helmet may be any receptacle that holds the electrodes in a position relative to the head of a wearer, or alternatively, electrodes may be taped or otherwise placed on the head. Earphones 102, goggles 104 and/or another display device are used to exhibit stimuli to a user, the stimuli used to vary measurable brain activity.

The electrodes 106 are electrically connected to one of an electrical stimulation device 150 or electrical measuring device (e.g., a sensor), such as by way of amplifier 152. The same electrode or electrodes may be disconnected from one such device and connected to another such device, such as by way of changing an electrical pathway (switch) or by physically disconnecting an electrical wire from one device, and plugging into another. Other devices, not shown, include force platforms (measure postural deviations of person), devices to alter the display on the goggles 104, and devices to alter the sound through the earphones 102, and input devices such as a computer mouse, keyboards, and joysticks.

Referring now to visual stimuli exhibited on a display device, such as the goggles 104 of FIG. 1, the visual stimuli produced may be an "immersive environment," for example a virtual reality 2- or 3-dimension moving "room" displayed through a virtual reality headset. The data collected from the balance plate, heart rate monitor, EEG, and so forth, can be used in conjunction with the visual stimuli for neurophysiological trauma assessment and/or rehabilitation training. The data collected from this component, as well as all other components may be linked with data collected from other components (e.g., EEG, ERP, ECG) for assessment purposes.

The system shown in FIG. 1 may further comprise a vestibular activation test (VAT) headset permitting a computerized test that monitors the vestibulo-ocular reflex (VOR) during natural motion. A VAT headset useful for the systems described herein may produce images and/or record eye movements. Images displayed in the VAT headset may be generated by computer-implemented instructions and transmitted via electrical impulses to the VAT headset via wireless or direct connection. Eye movements may be recorded by way of the VAT headset. The VOR is a reflex eye movement that stabilizes images on the retina during head movement by producing an eye movement in the direction opposite to head movement, thus preserving the image on the center of the visual field. As ocular trauma is often concomitant with traumatic brain injury, this component allows additional assessment of injury.

The measurements of electrophysiological data of a patient may include measurements acquired from dry or wet sensors or functional near infrared spectroscopy (fNIRs) optical fibers that send light into the scalp at wavelengths in the range of 650-850 nms. The sensors and/or fNIRs may be attached to the non-invasive brain stimulation or modulation helmet/cap described herein.

Moreover, for clarity purposes, as used herein, a patient may refer to an individual under direct care or supervision of a doctor, but a patient is not so limited and may further include any suitable user or client wherein measurement data is acquired and analyzed as described herein. For example, a patient may include non-medically related uses, such as an athlete and the review/analysis of electrophysiological data of an athlete to analyze possible concussion data. Another example of a patient may be soldiers with the review/analysis of electrophysiological data of the soldiers to analyze data relative to possible traumatic brain injury or post traumatic stress disorder.

Figure 2:
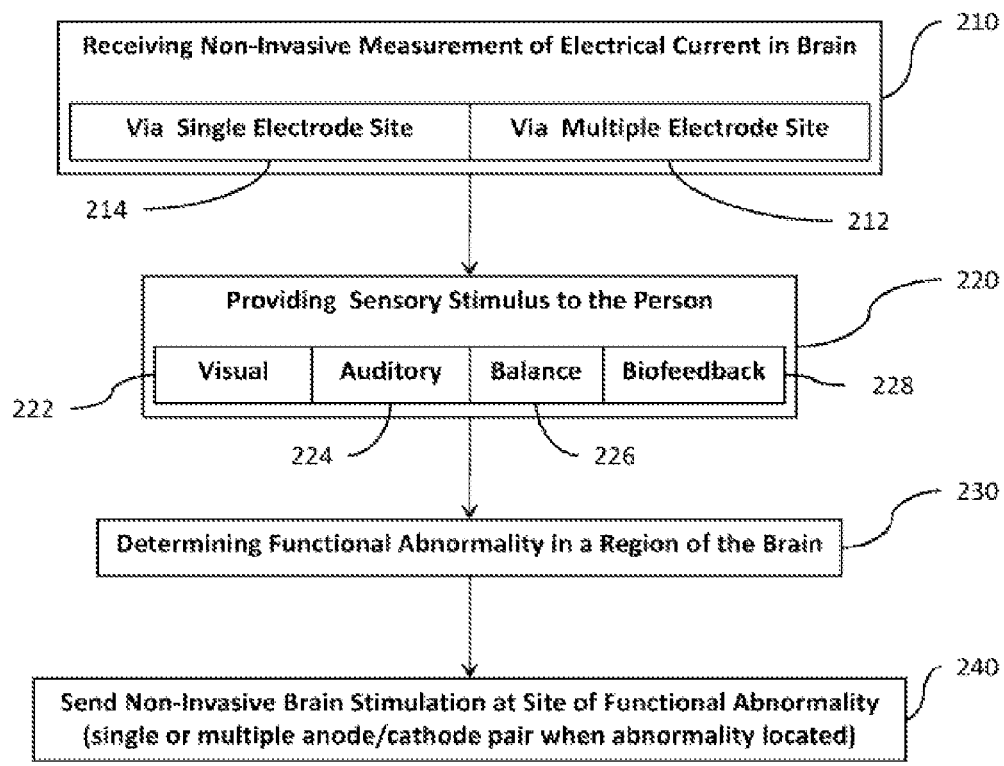
FIG. 2 illustrates one embodiment of a block diagram of a method for carrying measurements.

FIG. 2 shows a high level block diagram of a method for acquiring the measurements. In step 210, non-invasive measurements are made of electrical current in the brain of a test subject. This is accomplished by way of electrodes placed on a test subject, such as in a helmet shown in FIG. 1. In this manner, EEG and ERP signals may be recorded, measured, and analyzed. A single electrode may be used to carry out the measuring in step 214, or a plurality of electrode pairs may be used in step 212. The position of the electrodes is known, and each electrode or a grouping thereof is placed over a definable region of the brain, the region defined by a person carrying out embodiments of the disclosed technology. The region is defined as a specific brain area of interest for the recording, as defined by a person carrying out embodiments of the disclosed technology and may be a region covered by a single electrode pair or as large as half a hemisphere of a brain. Electrodes may also be grouped into clusters, such as with a single anode surrounded by three or more cathodes, or a single cathode surrounded by three or more anodes. Such clusters are electrically connected, such that electric current flows non-invasively through the proximal tissue from anode(s) to cathode(s), stimulating the brain (stimulating, herein is defined as passage of electrical current through the brain and includes increasing or decreasing neuron activity at a site).

While conducting step 210, typically, step 220 is also carried out which comprises providing sensory stimulus to a person. This may be done by way of, for example, the goggles shown in FIG. 1 for a visual stimulation 222, auditory stimulation 224, balance stimulation 226, biofeedback measurements 228, or other sensory stimulations known in the art. Definitions and examples of various types of such stimulations are provided above, before the description of the figures.

Stress tests and peak performance tests may also be performed to determine, for example, how many times a minute a person is able to respond to a stimulus, or how long a person can hold his/her breath or balance on a force platform, etc.

Based on the electrical measurements, that is, EEG or ERP measurements, an abnormality in a region of the brain is determined in step 230. An abnormality may be any of the following: electrical activity which is too infrequent, too frequent, too low in amplitude, too large in amplitude, an improper pattern of electrical activity, inter-intra-hemispheric connectivity, electrical activity in the wrong portion of the brain for the stimulus given, or the like.

In step 240, based on the located functional abnormality, non-invasive brain stimulation (such as tDCS) is administered at the region of the Abnormality. In certain cases, the same electrode which was used to measure the electrical impulses within the brain is used to administer tDCS or other electrical stimulation. In this manner, accuracy of the stimulated region may be assured, as there is no difference in the physical location on the head where the existing electrical impulse was measured, versus where the new electrical stimulation is administered. The place of administering may be as little as a single anode/cathode pair (or cluster), or may use multiple anode/cathode pairs (or clusters).

Figure 3:
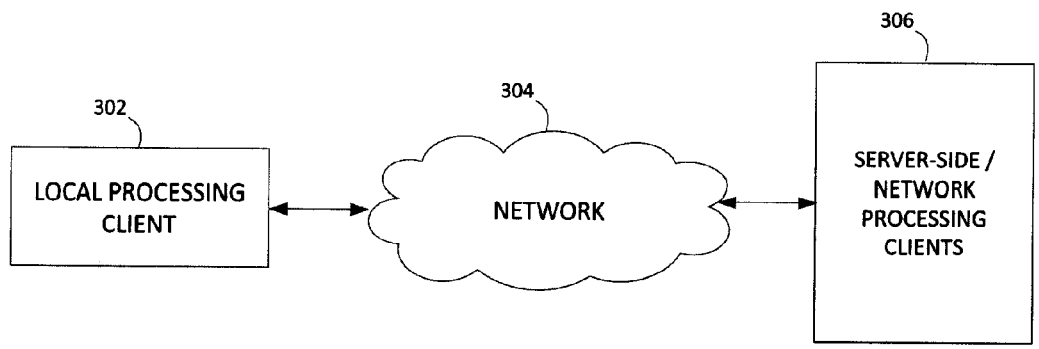
FIG. 3 illustrates one embodiment of a processing environment for the measurements and processing described herein.

Whereby the device of FIG. 1 provides for collection of data, FIG. 3 illustrates an embodiment of processing environment providing for the remote database and data analysis method and system operations. In this system, the local processing client 302 may be any suitable local processing device including but not limited to the collection of measurement data, and/or one or more processing systems for executing interface operations. For example, in one embodiment the local processing client may be a personal computer or a tablet computer having a browser or application for executing the interface functionality described herein.

The network 304 may be any suitable network providing communication thereacross. In one embodiment, the network 302 is an Internet connection across a public access network, wherein it is recognized that the network may include a private and/or secure network, as well as network exchanges via one or more service providers. The network 304 operates to facilitate the communication of data between the local processing client 302 and the server-side network processing clients 306.

The server-side network processing clients 306 may be any suitable number of network-processing devices. In one embodiment, the client 306 may be a dedicated processing server, wherein in another embodiment, the client 306 may be any suitable number of distributed computer resources for processing operations as described herein.

Figure 4:
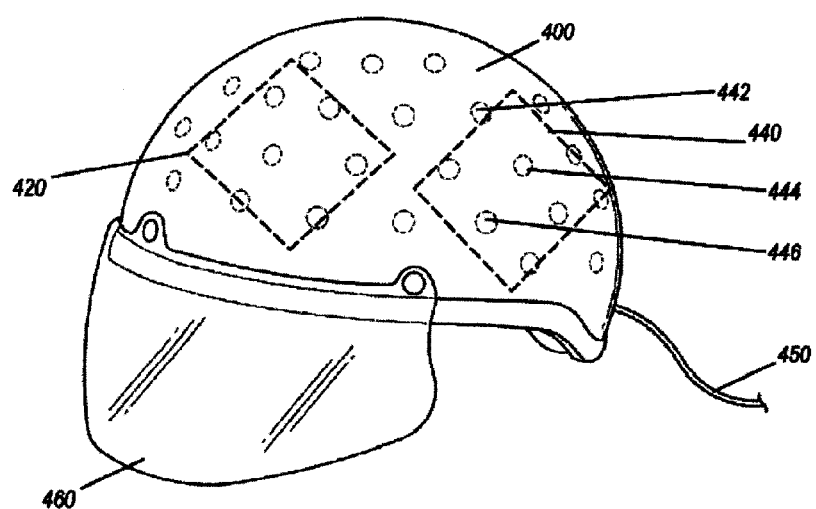
FIG. 4 illustrates one embodiment of a helmet with electrodes used in the taking of measurements.

As part of the data collection for client 306 processing, FIG. 4 shows a perspective view of a helmet with electrodes used in embodiments of the disclosed technology. The helmet 400 comprises multiple electrodes, such as electrodes 442, 444, and 446. As can be seen in the figure, a plurality of electrodes are spaced apart around the interior of a helmet or other piece of headgear and are adapted for both reading electrical activity from the brain of the wearer and delivering new impulses. That is, by way of a single electrode, plurality thereof, cluster of electrodes, or plurality of clusters, a joint brain electro-analysis and transcranial direct current stimulation system (tDCS) comprises a plurality of spaced-apart removable and replaceable electrodes arranged in an item of headgear. An electroencephalography device (such as an EEG) is wired to each of the electrodes, as is a transcranial direct current stimulation device (at the same time or alternating by way of a switch or plugging/unplugging a cable between the devices).

A cable 450 allows for electrical connectivity between the electrodes and either or both of a tDCS and EEG device. Further, a viser 460 is integrated with the helmet in embodiments of the disclosed technology for optical stimulation (e.g. a video monitor).

Upon measuring an electroencephalography anomaly in a brain region with the electroencephalography device, transcranial direct current stimulation is engaged to at least one anode and at least one cathode electrode to the brain region where said anomaly was measured. Additional devices such as a force plate, visual stimuli utilizing interactive games and tests, and the like, may be utilized.

The data collection techniques and operations, as described in U.S. patent application Ser. No. 13/742,066 and U.S. Pat. Nos. 8,380,316 and 8,239,030 are herein incorporated by reference.

The data is collected and thus provided to one or more remote data processing systems. These remote data processing systems may be connected via a networked connection, including in one embodiment an Internet-based connection. In additional embodiments, the networking may be via a private or secure network. Wherein, it is noted that Internet-based connections include the processing of security features with the data, to insure the privacy of the data during transmission.

For example, one embodiment may include a data collection computing device, such as a personal computer or other type of processing device, operative to receive the electrophysiology data. The processing device therein provides for the encryption or inclusion of security features on the data and the transmission to one or more designated locations. For example, one embodiment may include the compression of the data into a ".zip" file.

Figure 5:
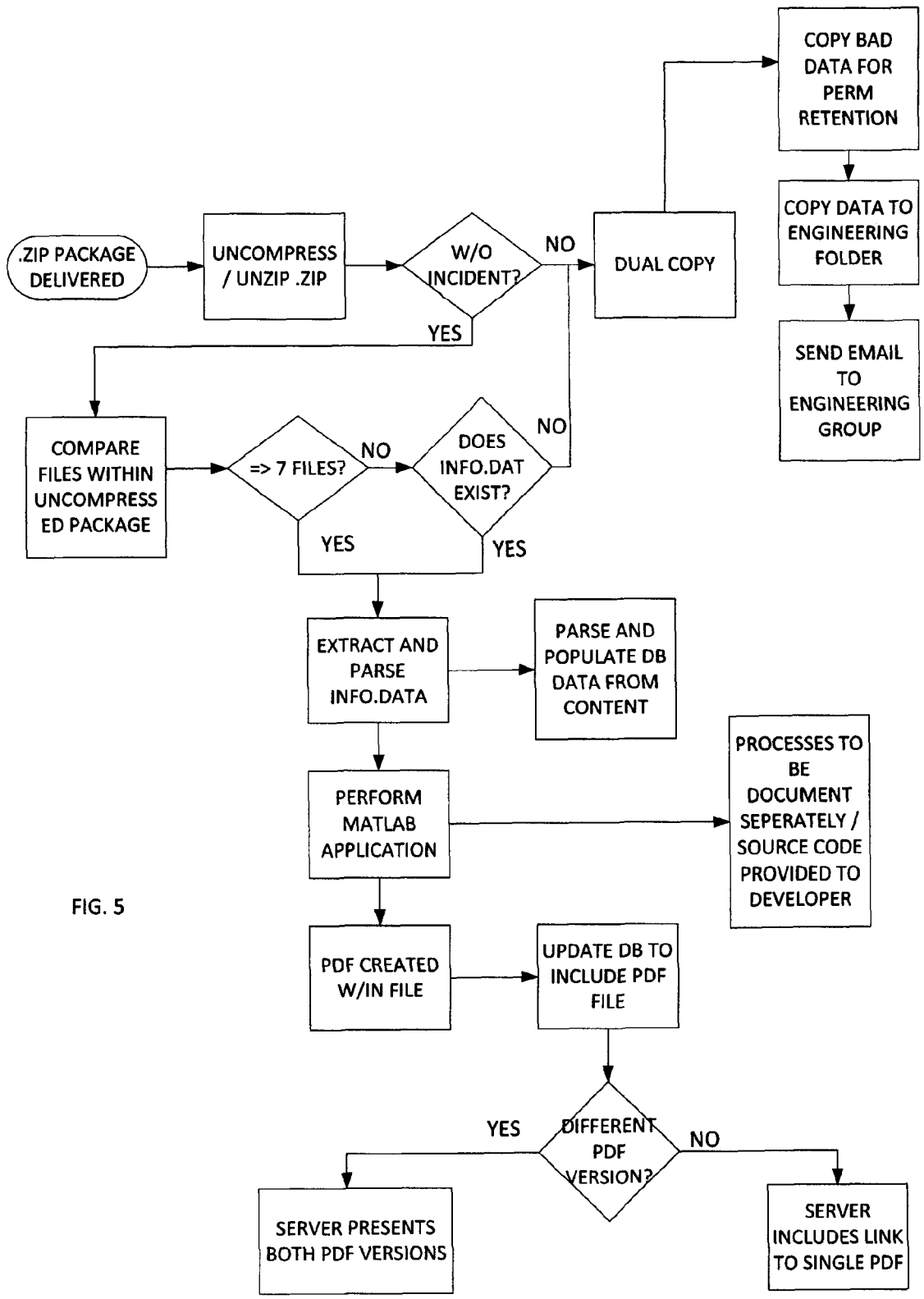
FIG. 5 illustrates one embodiment of a data flow cycle.

FIG. 5 illustrates one embodiment of the server-side processing. In this embodiment, the client side includes the collection of the data and the transmission to the server. The compressed file is then uncompressed. A check determines if the uncompressed file is error-free. If no, a check determines if a there exists a dual copy of the data already on the network.

In one embodiment, the network transmission may include transmission redundancies including sending or routing data to the server using multiple transmission paths or routes. If there is not another copy, the system may then seek to improve its operations by copying the bad or corrupted data to a corrupt data file and sending such information to a system engineer. Whereupon, that corrupted data may be examined to determine techniques to improve compression and/or decompression.

If the decompression is proper, one technique is to then count and/or document the files within the uncompressed package. In one embodiment, a predetermined file number is set established as a threshold to begin the processing of the data files. In this embodiment, the predetermined number is 7 such that if greater than 7 files, extract and parse the info.data. If less than 7 files and no info.data file, this may indicate bad data on the client side data collection, generation or transmission, therefore the information is again submitted to a quality control group for proper refinement of the processing system.

With the inclusion of the info.data file, the server side processing system operates to parse and populate database data from the content. It is recognized by one skilled in the art that the server side or network side processing may be performing in one or more local or distributed computing environment. Similarly, the database and data storage thereon may be performed in a local data storage device or the database may be disposed across one or more networks in a distributed environment.

From the extracted and parsed info.data data, the server further executes one or more software applications for the performance of data analysis and computational processing. In one embodiment, this software includes Matlab® applications working in conjunction with the primary data processing code in code language (e.g., C# and C++) specifically designed to process the data in a fully automated manner with flag features that select data analysis results for human review. In this processing, the collected data is then available for execution of analysis routines. The Matlab® Software is currently available from MathWorks, Inc.

The server further provides for the storage of the data and retention of data information. In this embodiment, the server creates a postscript formatted file, such as a PDF file and the database is then updated to include storage of this information. In one embodiment the database further includes enhancements to maximize storage, including determining if the data to be stored is duplicative. If the data is duplicative, a single data link can be provided, but if the data is not duplicative, then separate access to the data is provided.

The data, including the measurement data and the analyzed data are then stored in the database, allowing for subsequent user access as described below.

Wherein the present system and method allows for network based computation of the data as described above, the method and system further provides for user access to the network data. The user may access the database via a browser or other type of access device or terminal. In one embodiment, the user may be presented access via a public network, such as the network, with the proper security or encryption components insuring safe data access and interaction. In another embodiment, the computing system may be a dedicated terminal on a private or secure network.

Figure 6:
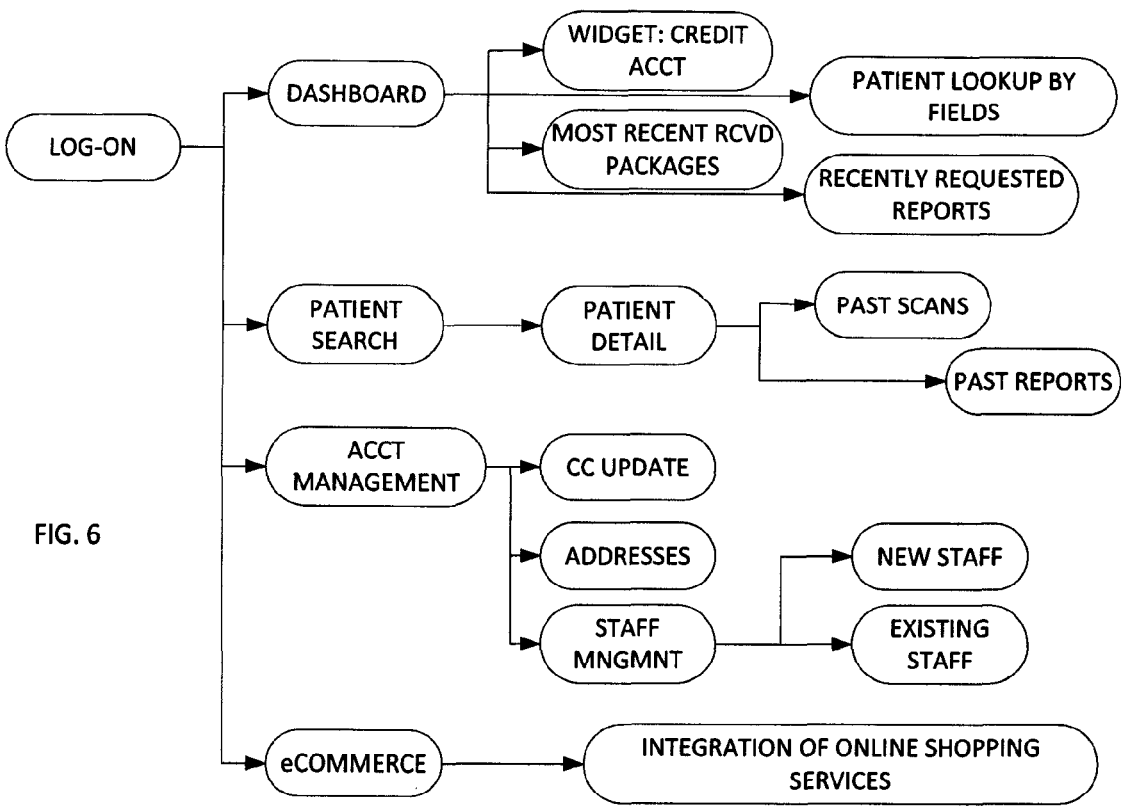
FIG. 6 illustrates one embodiment of a data flow diagram illustrating server-side operations.

In the data flow diagram of FIG. 6, the client (user) logs into the network. This may be performed using standard logging techniques recognized by one skilled in the art. The user may therein be presented with a dashboard.

The graphical display of the dashboard may be via an applet or other local or network based executing software. In the dashboard, the user can execute a software application (widget) to manage account features, the user can execute a search or look-up feature for patients, as well as other functions. One additional function is the inclusion of a "most recent received packages" tab allowing for a user to quickly access and review recent transactions. Similarly, another tab may be recently requested reports, providing a history of reports the user has requested.

In a typical embodiment, the user or client is a doctor or other medical specialist having the ability to review, understand and advise a patient based on the data generated in the reports. As noted above, the data generated in the reports relate to the electrophysiology data acquired from patients.

Patient searching functionality can include searches based on patient details, scan data and/or past reports. Account management functions include various processing operations to manage the user account, including for example staff management and financial transaction oversight.

Another feature of the interface includes electronic commerce or the ability to access commercial features. For example, a user may wish to upgrade electrophysiology equipment, therefore the user can be directed via the interface. In another example, the user may review the patient data and appreciate that further refinement of the testing or different types of tests need to be performed to better fine-tune the results, such that medical equipment can be recommended and made available via the interface.

In one embodiment, the present method and system uses a data nomenclature to better process the data. This exemplary embodiment includes the following naming standard to shorten, simplify and identify four primary characters of a single scan session. Using an example of CA121P2914S2, the breakdown of the four characteristics are as follows: (CA121P2914S2)

CA=The First two characters of the session identifier represents the client's company state code.

121=the clients numeric value assigned to the client's company name. Other possible values include 121-1, 212-2, etc. This would occur if the client has more than one device.

P2914=Patient ID uniquely assigned to a patient at the device level.

S2=Session Number.

In one embodiment, both the Patient ID and the Session Number are assigned to the patient at the time of registration at the device level. Since the devices maintain independent database, both the Patient ID and Session Number are unique to the testing device only. As a result of this scenario, a lookup process utilizing data extracted from info.dat may be required to perform a lookup on the master database to validate there are no other patients that contain the same data based on the data prior to new record creation.

Another aspect of the invention relates to Payload Delivery, defined as the compressed and encrypted contents uploaded from a testing device to the network location. One embodiment of data upload uses known secure file transfer protocols (SFTP), such as the address sftp.evokeneuroscience.com.

Another aspect is the included Server Side Report Generator Application and the requirements associated therewith. Using the included workflow the requirements of the server side application are as follows:

Item 1: The Application must allow administrators to point to 4 unique UNC pathways. (a) Inbound SFTP Watch Folder—Will be used to keep a constant monitor of the newly received payloads. (b) Permanent Retention—Will be used to store all payloads regardless of success disposition. (c) Engineering Troubleshooting—Will be the destination location, which will COPY payload source data that error out during the report generation. And (d) Clinician Review—Will be the destination location, which will COPY payload raw data, generated source data, and generated Microsoft Word document(s) for review by the clinician.

Item 2: The application will maintain a constant monitoring of the SFTP Watch Folder mentioned in item 1.a. The monitoring process will be required to monitor the size grown of payloads as the payloads are delivered. Any payload that is growing cannot continue to the next step until the payload delivery is complete and file size is static.

Item 3: The application will decompress and decrypt completed payloads to the permanent retention location outlined in the permanent retention above.

Item 4: In addition to the newly decompressed files, the application will MOVE received payload compressed file to the same new permanent destination as created in item 3. If, the application receives an error during the item 3, an additional copy of the payload must be delivered to the engineering folder outlined in item 1.c. Following the delivery of the copied payload, an email announcement must be delivered to a monitoring distribution group.

Item 5: Upon completion of item 4 (without incident), the Application will count the number of payload contents to insure a minimum of 6 files. (a) IF the count is LESS THAN 6 files, perform same error workflow outlined in 4.a and 4.a.1. (b) In tandem to the error reporting of 5.a, determine if received payload contents includes an info.dat file. IF info.dat exist, perform item 6.

Item 6: Application will extract and parse data elements from the info.dat file from each payload. The following contents will be used to populate a database stored using a server (e.g., SQL 2008). The fields include any number of data fields including but not limited to: Fields Include; Unique Code; First Name; Last Name; DOB; Test Date; Test Time; Subject Age; Gender; Handedness; Symptoms; and Medications.

The complete system consists of a wireless amplifier equipped to record artifact free electrical signals from the brain and heart and also position in space using a nine or greater accelerometer. This same device is configured to deliver electric current back to the sensors that are in contact with the scalp in order to facilitated non-invasive brain stimulation. Sensors make contact with this skin using either dry sensors or electro dermal gel or saline impregnated sensor for consistent sensor to skin connectivity measured by impedance.

The software provides for automated data collection using script software and self-guided instructions. The software sends the resulting data for algorithm processing either on the CPU or on a dedicated secure server through an internet connection. This data is processed on the CPU and processed either on the installed database and processing software or transmitted to the cloud-based server where processing takes place.

The data analysis is returned in a report format showing physiology graphics and interpretive results from which the user can make intervention or diagnostic decisions. Several comparison databases can be selected from within the software to provide a comparison measure for the data analysis. Pre-set EEG training protocols (e.g., theta:beta ratio training for attention; alpht:theta ratio training for relaxation) are configured for automated home or clinic based training.

Individual baseline data can also be utilized so that the individual's data can be compared to an earlier data sample. An example of this is a professional athlete having his or her pre-season baseline that is used for comparison following a concussion. This is particularly useful for single-subject design research of change over time and intervention results. Group databases such as peak performance or pathology comparison databases (i.e., Alzheimer's disease sample database) are also available for selection and data comparison. Intervention options include real-time noise and artifact removal algorithms that permit EEG and ECG training devoid of movement and other disruptive artifact or signal noise. Individual differences from the selected comparison database permits specific or individually derived interventions as non-invasive brain stimulation (e.g., tDCS/tACS) and brain computer interface (sLORETA/eLORETA brain computer interface, wavelet time-frequency neurofeedback, event-related potential neurofeedback; Brodman Area selection, neurofeedback, neuro-network brain computer interface) and peripheral biofeedback such as heart rate variability biofeedback).

The brain computer interface or neurofeedback can include any number of operations or techniques, including for example low resolution brain electromagnetic tomography source localization feedback and surface electroencephalography amplitude or phase or coherence feedback.

The user receives report and intervention information from cloud-based server interface or from optional embedded software on the CPU for usage where internet connectivity is not possible.

The results of the data analysis include a protocol that directs the non-invasive brain stimulation sensor placements and current parameters. These stimulation protocols can be manually or automatically selected to provide the user with both brain compute interface training and brain stimulation or brain modulation interventions.

The rapid assessment and re-assessment of the brain and other measures included in the physiology measurement battery allows for rapid determination of brain computer interface training location and frequency protocols and also brain stimulation or modulation using electric current. The re-assessment quantifies the difference from the baseline measure in order to generate a report showing the change made by either or both brain computer interface and electric current brain modulation.

The re-assessment then provides an updated intervention protocol. Protocols will vary based on the assessment results such that the different locations on the scalp may be stimulated with different polarity at the sensor and with more or less milliamps than one another. Users can manually define scalp location, polarity at the sensor, and milliamp levels and duration at each location. Users can also select from pre-defined protocols to increase or decrease regional neuronal activity.

The same data analysis report provides illustration and instruction on the current flow through the brain tissue in order to further quantify the cortical excitability relevant to the users clinical or performance intent. Current flow reporting aid the user with further and more specific brain modulation targeting protocols using Talairach locations and Brodmann Areas. The availability of the data analysis and reports on the web portal allows for telemedicine access and review.

Remote access to data allows for international experts to guide brain assessment and training. The user can generate post-treatment measures whether the intervention was brain computer interface, targeted multiple-sensor non-invasive brain stimulation or modulation, or user defined (e.g., drug trial) interventions. The rapid reporting of functional measures aid the user to determine the brain function changes from the interventions in a rapid and reliable manner.

The sensors permit real time stimulation with electrical current and simultaneous recording of EEG using signal filters that remove the electrical stimulation and permit only the EEG and event related potentials to be recorded and processed. This feature permits the user to combine targeted brain stimulation with brain computer interface training using real time artifact correction. Simultaneous neurofeedback with stimulation allows for data analysis showing the focal changes or modulation in the brain from the individual or combined intervention modalities.

Figure 7:
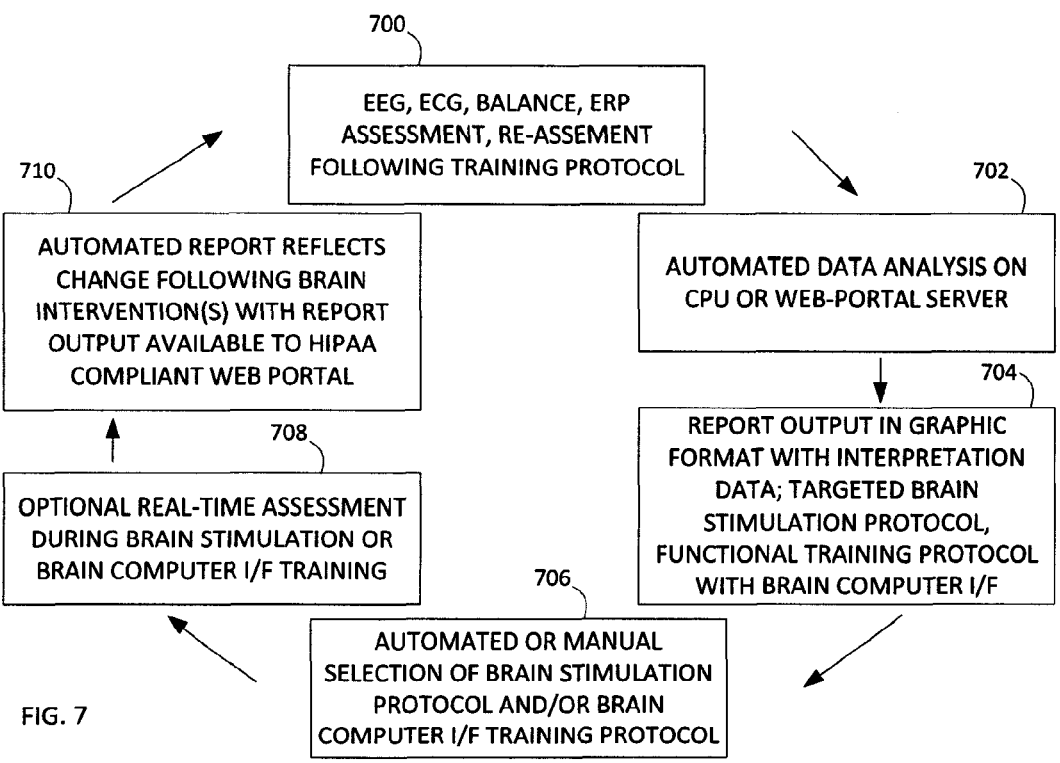
FIG. 7 illustrates one embodiment of a data flow diagram for a user-access to the database or network functionality.

FIG. 7 illustrates a circular data flow diagram representing the circular operations described herein. The steps are described in greater detail herein, wherein FIG. 7 provides a high level overview of one embodiment of the operation sequences.

Step 700 includes the assessment and re-assessment protocols, such as EEG, ECG, Balance, ERP, etc. Step 702 is the automated data analysis on a CPU or networked server. Step 704 is the report output, which may include output in graphical format with interpretation data. The report 704 may further include targeted brain stimulation protocol, functional training protocol with brain computer interface.

Continuing in the cycle of FIG. 7, step 706 is the automated or manual selection of brain stimulation protocol and/or brain computer interface training protocol. Step 708 is an optional real-time assessment during brain stimulation or brain computer interface training. Step 710 provides automated reporting that reflects changes following brain intervention(s) with report output, which can be available to a user including HIPAA-compliant web or network portals.

While the data collection occurs on the client-side, the server side processing allows for enhanced processing operations, including: (1) receiving payload files from client; (2) validating the payload files; and (3) generating one or more report files (e.g. PDF format) for the client to download or integrate into electronic medical records software.

To accomplish these goals, the processing is divided into two parts; each part implemented as separate applications. The applications are executed on the server-side 306 as noted in FIG. 3.

Figure 8:
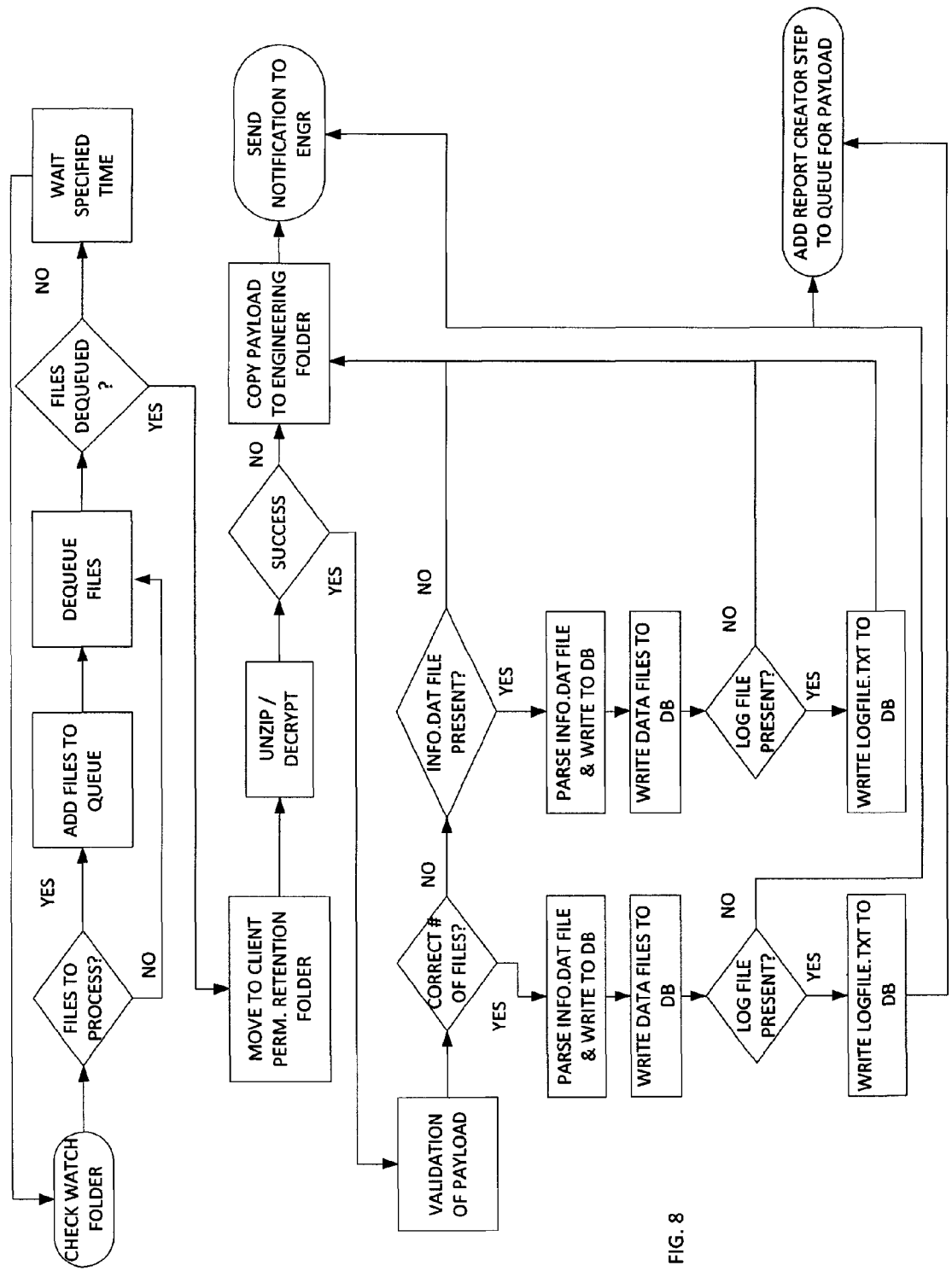
FIG. 8 illustrates one embodiment of a data flow diagram for a server-side payload file processing operation.

The first application handles receiving the payload files and validating their contents. The second application will handle the creation of the report file (e.g. PDF). FIG. 8 illustrates a data flow diagram of the process flow of the payload file processing application.

The application monitors the designated folder on the client's ftp server. When a payload file is uploaded, the application adds that file to the queue table in the database. The application de-queues a file and will move the folder to the client's permanent storage folder. The payload is unzipped and decrypted, creating a new folder for the payload within the client's permanent storage folder. The contents of the payload are validated against the business rules specified in Major Application Components, Validation section below.

Information from one of the files expected in the payload (info.dat) is parsed and stored in the Patient table in the database. All of the data files of the payload are stored in the SessionFile table in the database. If no errors occur during this process, information about the payload is saved in the SessionQueueState table in the database.

The application uses a notification service to alert specified parties when an error occurs during processing or when the payload file violates a business rule. The notification service sends an email to the specified email address including a brief description of the issue encountered.

Figure 9:
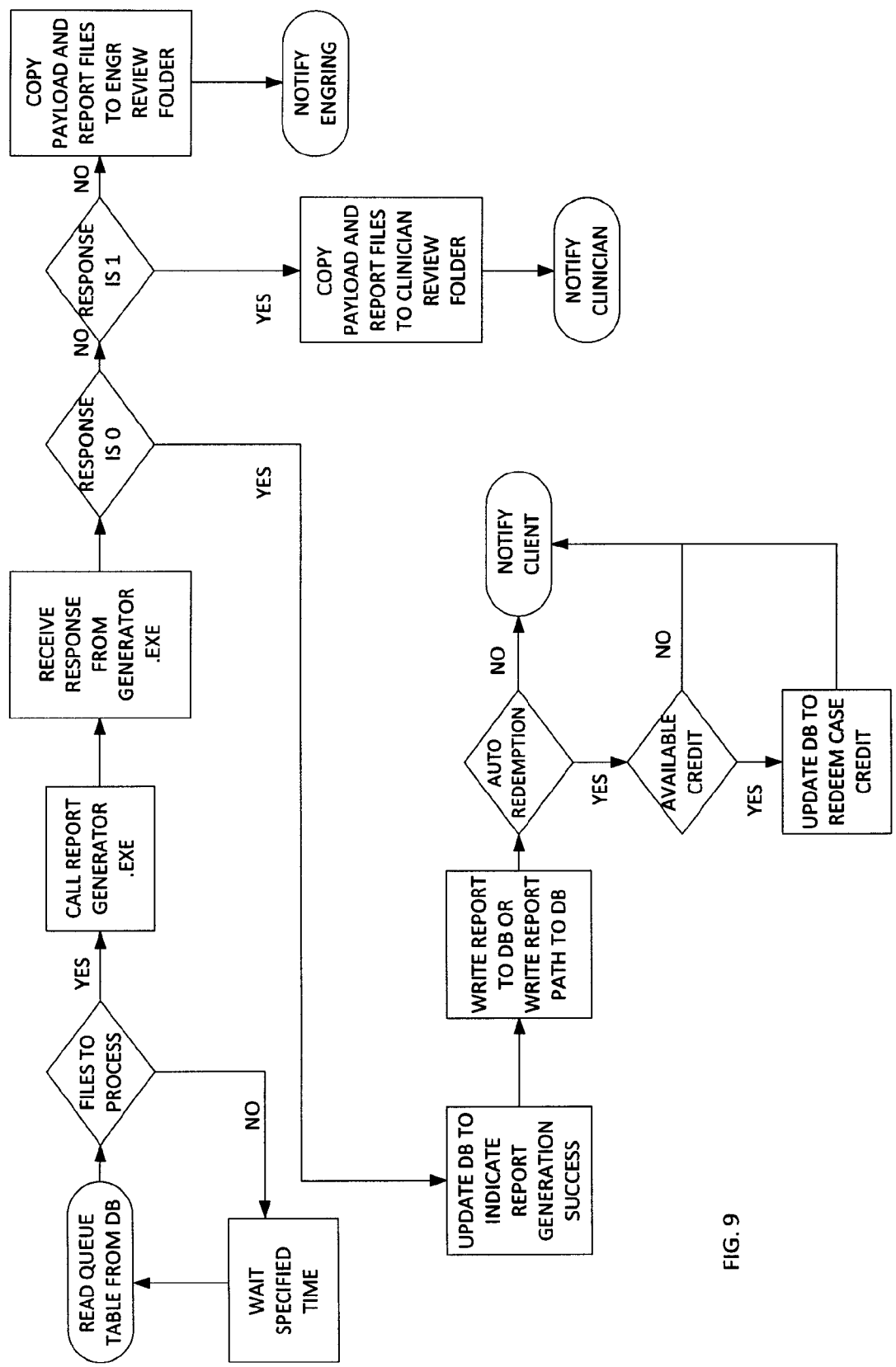
FIG. 9 illustrates one embodiment of a data flow diagram of a report creator processing operation.

The second application is a report creator. Various embodiments provide data flow operations. FIG. 9 illustrates a first embodiment of a report generator. In this report generation, a successful output is the notification of the client. Whereas, in the event error(s) occur, the process data flow includes notifying a clinician and/or notifying engineering, which works to assist in process complications.

The first process of the report creator application monitors the report request queue table in the database. A new row in the table indicates that a report needs to be created. Using information in the queue table, the report creator executes the report generation application. The report generation application returns a code indicating success or failure.

If the return code indicates success, the client who submitted the payload from which the report was created is notified that the report is available. If the return code indicates an error, the application uses a notification service to alert specified parties when an error occurs. The notification process is the same mentioned in the payload processing above.

In one embodiment, the data analysis included within the report generation includes multiple processing features. A first feature is the EEG signal data, subject self-report test item data, ECG signal data, accelerometer data is combined and then uploaded from the local CPU to the network processor using a Watch Folder. As described herein, the data is acquired using various acquisition techniques applied to the patient, including running test or other routines on the patient with the measurement devices. The data may be encrypted for data and patient information security.

A second feature of the report generation is that the bundle of data is then sorted at the server level and each data type is processed for data integrity and compared to normative databases, or the same individual's pre-test data comparison, or to a special population comparison database (e.g., Alzheimer Disease, Military Special Operations). In one embodiment, the EEG and ECG and accelerometer data are processed initially with artifact and movement detection and removal software that includes independent component analysis (ICA) algorithms. The post-cleaned or artifact corrected data is then processed in a manner to display graphically the unique characteristics of the electrophysiology data and based on the database comparison information there is added interpretation comments and intervention suggestions that included: medications likely to be effective, supplements likely to be effective, non-invasive brain stimulation protocols, neurofeedback protocols.

A third feature of the report generation includes that the completed report and all measured and depicted physiology and behavioral data is then run through algorithms that will flag the report for clinician review if particular values are outside normal ranges. If flagged for review, notice is give the selected clinical and engineering personnel to review and re-upload to the client web portal. If the reported values are initially within normal ranges the software will transfer the completed report to the client web portal where via username and password the client can access the written report in a readable and downloadable format (e.g., PDF) for printing or upload into electronic medical records.

In one embodiment, the entire process of initial data transfer to report availability is less than one minute and local data analysis can be configured to permit faster assessment results in order to facilitate a train-test-retrain model for clinical or research use.

In one embodiment, the servers-side application uses, in-part, Matlab® components with report generator code to automatically process physiology data and create data analysis reports.

Figure 10:
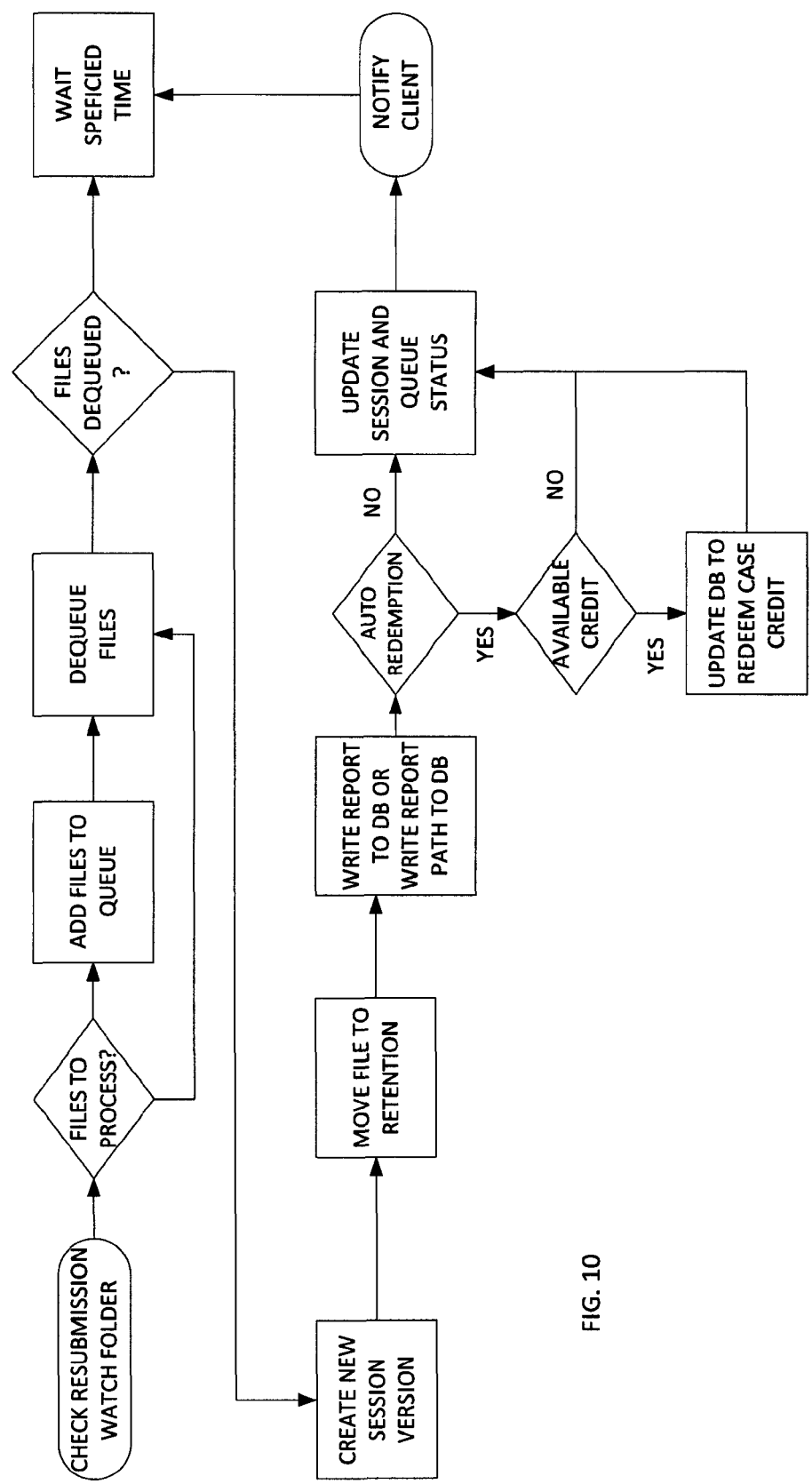
FIG. 10 illustrates another embodiment of a data flow diagram of a report creator processing operation.

FIG. 10 illustrates a data flow diagram of a report generation for a clinician resubmission. The second process of the report creator application monitors the clinician resubmission watch folder. A report file in this folder indicates that a clinician has corrected a report file and wants to submit it to overwrite the original report created for the session. The clinician creates the updated file (e.g. by saving an updated Word report file in PDF format) and then moves the updated file into the clinician resubmission watch folder.

The report creator application updates the database with information about the corrected report file (Session and SessionFile tables). The report file is moved to the payload's permanent retention folder and replaces the previous version of the report file. If this process is successful, the client who initially submitted the payload is notified that the report is available.

Figure 11:
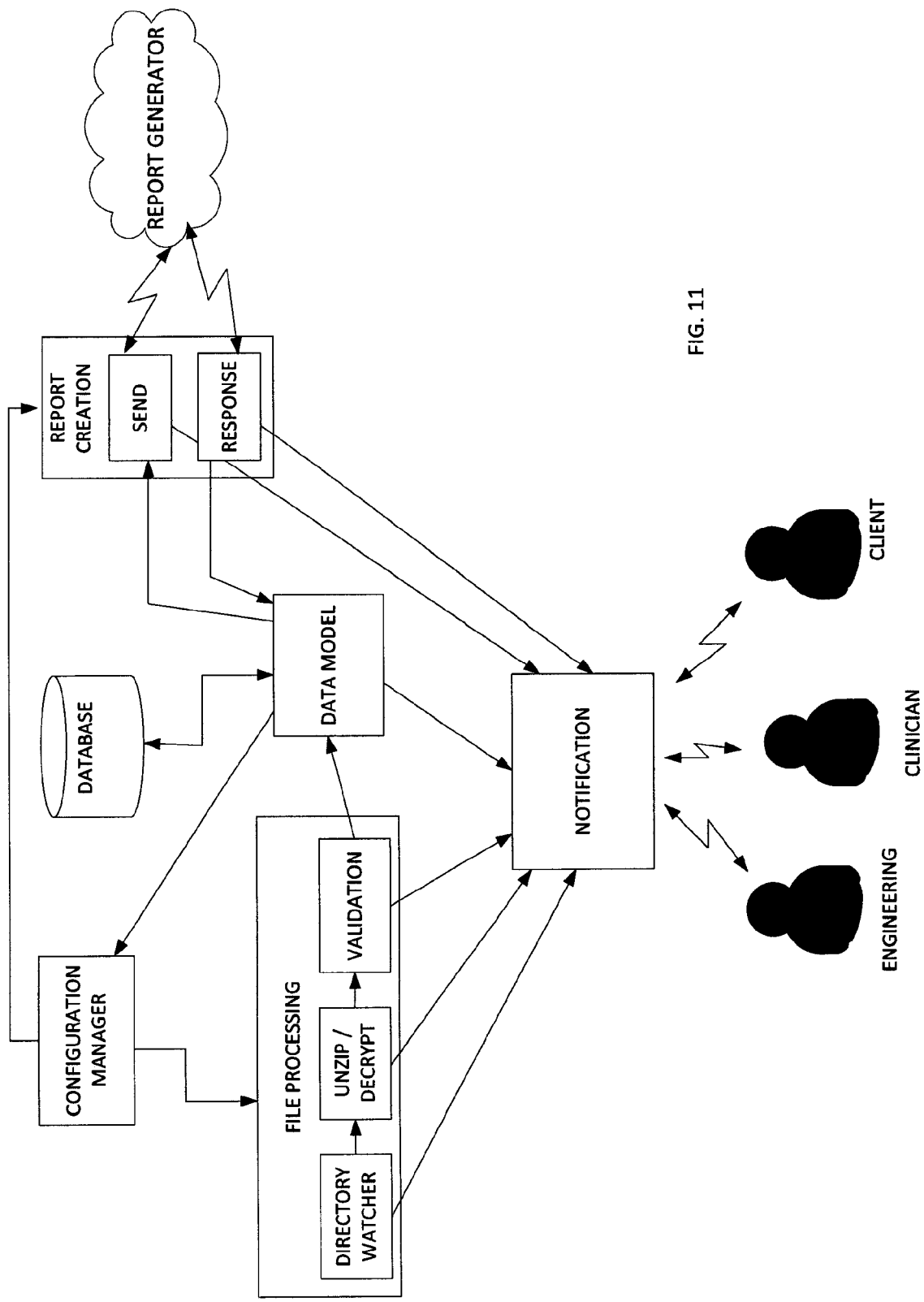
FIG. 11 illustrates one embodiment of multiple server-side applications operative with a plurality of users.

FIG. 11 illustrates a system diagram of the application components described above. FIG. 11 illustrates the three exemplary users, engineering, clinicians and clients. FIG. 11 illustrates the interactivity for the two server applications described above, applications for data collection and report generation.

A first component is the configuration manager, which provides configuration settings for the service side applications to execute successfully. It reads configuration settings from the database or a configuration file and provides the values to the applications. The specifications for the configuration manager component include: (1) read information from the Config table in the database using the Data Model; (2) provide value of settings by setting name; and (3) setting value provided in the configuration file take priority over that same value found in the database.

A second component is a directory watcher. The primary responsibility of the directory watcher component is to monitor the designated folder on the SFTP server for payload files. It moves the payload files to the appropriate permanent retention folder once the payload file upload is complete.

The specifications for the directory watcher component includes: (1) configuration parameter to indicate directory to be monitored for incoming payload files; (2) configuration parameter to indicate top level directory for permanent client storage; (3) configuration parameter to indicate top level directory for engineering to be used if the payload processing causes an error or violates a business rule; (4) verify that payload .zip file upload is complete; (5) verify that payload ftp log file is present for a new payload; (6) if a resubmission, payload name will be modified to include a version number; (7) use data model to communicate with database in determining correct version number; (8) move the payload file(s) to the appropriate client folder; (9) use the data model component to insert a row in the payload database table to indicate a new payload file has been received; (10) use the notification component to alert engineering if there are errors with any of the above steps; (11) copy the payload to the engineering directory if there are errors with any of the above steps; and (12) use Microsft.Net FileSystem objects to monitor the inbound directory, move files, rename files.

A third component is the Unzip/Decrypt component. The unzip/decrypt component will unzip the payload .zip file into the directory in which the file resides. If decryption is necessary, this will be done in the same directory. Specifications for this component include: (1) unzip .zip file in current directory; (2) decrypt file in current directory; (3) use the notification component to alert engineering if there are errors; (4) copy the payload to the engineering directory if there are errors; and (5) application uses the DotNetZip library to unzip the payload files.

Business rules are checked in the validation component. The following are the current business rules: valid number of files in payload; payload includes info.dat file; and new payload includes ftp log file (only a warning if missing, processing for the payload continues).

The specifications for the validation component includes: (1) configuration parameter to indicate expected number of files in payload; (2) count number of files in payload; (3) check file names to verify that info.dat is present; (4) check to verify that logfile.txt is present if this is a new payload; (5) use the notification component to alert engineering if there are violations of business rules or if there is an error in any of the above steps; (6) copy the payload to the engineering directory if there are errors with any of the above steps; and (7) use Microsoft.Net FileSystem objects for file checking.

The data model component will communicate get, insert and update commands to the database. The other components of the application will send necessary database requests through this component. The specifications for this component include: (1) classes that model the database tables needed for the applications; (2) entity Framework ORM tool will be used to create these classes; and (3) database tables to be modeled are listed below in the database section The report creator component checks the database report request queue to see if any reports need to be created. It calls the report generator executable with the appropriate parameters. The report generator returns a code to indicate the success or failure of the report generation. The report creator also monitors the clinician resubmission watch folder to see if there any resubmitted reports to process.

The report creation component specification includes: (1) configuration parameter to indicate location of report generator executable; (2) database field to indicate location of template file required for the report generator; (3) call report generator executable and wait for response; (4) notify engineering, clinician or client based on response code (e.g. 0=success, notify client report is ready, 1=failure, notify clinician that review is needed, >1=failure, notify engineering that review is needed); (5) if success, check automatic credit redemption flag to see if client should be charged a credit for the report automatically; (6) use data model to update status of payload if report created successfully; (7) use notification component to notify appropriate party if there are errors; (8) configuration parameter to specify clinician resubmission watch folder; (9) use data model to correctly version session for resubmission; (10) move new PDF report to correct retention folder; (11) use data model to update report in the database; and (12) Microsoft.NET file system objects are used to move the report files.

The notification component's primary responsibility is to send notification emails to the appropriate party. Specifications for this component include: (1) configuration parameter to indicate engineering email address; (2) configuration parameter to indicate clinician email address; (3) configuration parameter for SMTP server name or ip address; (4) configuration parameter for SMTP port; (5) need client email address—from database or in constructor; and (6) send email via SMTP An engineer or clinician can resubmit payload files that result in errors. The resubmitted payload includes a trailing "-C" or "-E" that is manually added to the first portion of the file name. The payload file is then manually copied to the SFTP directory watched by the directory watcher component. When the file is processed, the file processing application is responsible for determining the correct version number for the file and renaming it accordingly.

Clinician review could require a new report file be created but would not require resubmission of the entire payload. The new report file can be resubmitted to the system by manually copying the new file to the clinician resubmission folder watched by the report creator component. The report creator application properly versions the new submission and moves it to the correct permanent retention folder.

The database can include any suitable data usable for the processing operations described herein. As part of the server side processing, the database may include the following data types/fields: client; configuration; credit; patient; processing nodes; session data; sessionfile data; sessionoutputstate; sessionReport; and FileHandlingStatus data.

Both server applications are configured to log error messages, warnings, information, and debug messages with several log methods. The messages can be written to a text file, the server's event log, a database table, or any combination of these methods. Logging of this information is useful in debugging errors that might occur in the application. Configuration settings will control if logging is turn on and what level of logging will be triggered.

The applications use NLog for logging. Each application has a separate configuration file for NLog settings (NLog.config). NLog is configured to write to a log file or to the windows event viewer. The log files are located in a logs folder within the folder where the application is located. By default, logging is turned off for each application.

Therefore, the herein described method and system improves upon electrophysiology measurement and training using a remote database and server-side analysis and measurement operations. Server side operations may be performed in response to executable instructions instructing one or more processing devices to perform processing operation. Such executable instructions may be stored in one or more computer readable media, as recognized by one skilled in the art, such as non-transitory computer readable media.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the disclosed technology.

What is claimed is:

1. A method for electrophysiological data analysis, the method comprising:
   acquiring electrophysiological data from a patient using non-invasive brain stimulation in an immersive environment, including detecting an abnormality region within a brain of the patient;
   receiving, via a networked connection, the electrophysiological data of the patient;
   electronically performing, via at least one network processing device, a data analysis on the electrophysiological data;
   generating at least one report based on the performing of the data analysis, wherein the at least one report includes determination of one or more intervention options for the patient;
   transmitting the report to a recipient device across the network connection for utilization with the patient; and
   applying stimulation to effect the abnormality region of the brain of the patient based at least on the report.

2. The method of claim 1, wherein the electrophysiological data includes at least one of: electroencephalography data, event related potential data, electrocardiography data, behavioral measures, and balance data.

3. The method of claim 2, wherein the electrophysiological data is acquired from the patient using a helmet/cap having at least one of: dry sensors; wet sensors; and functional near infrared spectroscopy optical fibers sending light at a wavelength range of 650-850 nm.

4. The method of claim 1 further comprising:
   receiving the electrophysiological data across a secure network connection, wherein the electrophysiological data is in a compressed and secure file format.

5. The method of claim 1 further comprising:
   generating at least one graphical elements with the at least one report, the graphical element based on the data on the performing of the data analysis.

6. The method of claim 1, wherein the intervention options include at least one of: non-invasive brain stimulations, brain computer interface or neurobiofeedback, and peripheral feedback, wherein the peripheral feedback includes at least one of: balance training and heart rate variability biofeedback.

7. The method of claim 6, wherein the brain computer interface or neurobiofeedback includes at least one of: low resolution brain electromagnetic tomography topography source localization feedback and surface electroencephalography amplitude or phase or coherence feedback.

8. The method of claim 1 further comprising:
   accessing a database having previous electrophysiological data of the patient;
   electronically performing, via at least one network processing device, a re-assessment of the patient based on the electrophysiological data and the previous electrophysiological data.

9. The method of claim 8 wherein the electrophysiological data of the patient represents changes from the previous electrophysiological data and the application of the one or more intervention options on the patient.

10. The method of claim 9 further comprising:
generating a second report based on changes between the previous electrophysiological data and the electrophysiological data.

11. The method of claim 10 further comprising:
determining at least one more second intervention options for the patient based on the second report.

12. The method of claim 10, wherein the second report includes a graphical display representing changes in a central nervous system and an autonomous nervous system of the patient based on the application of the one or more intervention options on the patient.

13. A system for electrophysiological data analysis, the system comprising:
a device for acquiring electrophysiological data from a patient using non-invasive brain stimulation in an immersive environment, including detecting an abnormality region within a brain of the patient;
a processing device disposed in a networked computing environment; and
a plurality of executable instructions, such that the processing device, in response to the executable instructions, is operative to:
receive, via a networked connection, the electrophysiological data of the patient;
perform a data analysis on the electrophysiological data;
generate at least one report based on the performing of the data analysis, wherein the at least one report includes determination of one or more intervention options for the patient;
transmit the report to a recipient device across the network connection for utilization with the patient; and
wherein, the device is therein operative to apply stimulation to effect the abnormality region of the brain of the patient based at least on the report.

14. The system of claim 13, wherein the electrophysiological data includes at least one of: electroencephalography data, event related potential data, electrocardiography data, behavioral measures, and balance data.

15. The system of claim 14, wherein the device includes at least one of: dry sensors; wet sensors; and functional near infrared spectroscopy optical fibers sending light at a wavelength range of 650-850 nm.

16. The system of claim 13, wherein the processing device, in response to further executable instructions, is further operative to:
receive the electrophysiological data across a secure network connection, wherein the electrophysiological data is in a compressed and secure file format.

17. The system of claim 13, wherein the intervention options include at least one of: non-invasive brain stimulations, brain computer interface or neurobiofeedback, and peripheral feedback, wherein the peripheral feedback includes at least one of: balance training and heart rate variability biofeedback.

18. The system of claim 17, wherein the brain computer interface or neurobiofeedback includes at least one of: low resolution brain electromagnetic tomography topography source localization feedback and surface electroencephalography amplitude or phase or coherence feedback.

19. The system of claim 13, the system further comprising:
a database having previous electrophysiological data of the patient; and
the processing device, in response to further executable instructions, is further operative to further comprising:
access the database to retrieve the previous electrophysiological data;
performing, a re-assessment of the patient based on the electrophysiological data and the previous electrophysiological data.

20. The system of claim 19 wherein the electrophysiological data of the patient represents changes from the previous electrophysiological data and the application of the one or more intervention options on the patient.

21. The system of claim 20, wherein the processing device, in response to further executable instructions, is further operative to:
generate a second report based on changes between the previous electrophysiological data and the electrophysiological data.

22. The system of claim 21, wherein the processing device, in response to further executable instructions, is further operative to determine at least one more second intervention options for the patient based on the second report.

* * * * *